United States Patent [19]

Enzer et al.

[11] Patent Number: 4,786,394
[45] Date of Patent: Nov. 22, 1988

[54] APPARATUS FOR CHEMICAL MEASUREMENT OF BLOOD CHARACTERISTICS

[75] Inventors: Steven Enzer, Brooklyn; Bruce M. Burgess, Ann Arbor; Jack S. Wyman, Ann Arbor; Ricky Hendershot, Ann Arbor, all of Mich.

[73] Assignee: Diamond Sensor Systems, Inc., Ann Arbor, Mich.

[21] Appl. No.: 14,208

[22] Filed: Feb. 5, 1987

Related U.S. Application Data

[63] Continuation of Ser. No. 770,740, Aug. 29, 1985, abandoned, which is a continuation-in-part of Ser. No. 713,435, Mar. 19, 1985, abandoned.

[51] Int. Cl.$^4$ .................. G01N 27/26; G01N 33/48
[52] U.S. Cl. .................. 204/401; 128/635; 128/DIG. 3; 204/403; 204/406; 204/407; 204/409; 204/411; 204/412; 364/497; 422/81; 436/52; 436/68
[58] Field of Search ............. 204/401, 403, 406, 407, 204/409, 411, 412; 128/635, DIG. 3; 422/68, 81; 436/47, 52, 68; 364/497; 73/1 R

[56] References Cited

U.S. PATENT DOCUMENTS

| | | | |
|---|---|---|---|
| 3,556,950 | 1/1971 | Dahms | 204/1 T |
| 3,763,422 | 10/1973 | MacPhee et al. | 422/68 X |
| 3,874,850 | 4/1975 | Sorensen et al. | 422/68 X |
| 4,109,505 | 8/1978 | Clark et al. | 73/1 R |
| 4,116,336 | 9/1978 | Sorensen et al. | 206/524.8 |
| 4,218,197 | 8/1980 | Meyer et al. | 417/442 |
| 4,225,410 | 9/1980 | Pace | 204/406 X |
| 4,415,534 | 11/1983 | Lundsgaard et al. | 422/58 |
| 4,424,276 | 1/1984 | Clark et al. | 436/50 |
| 4,452,682 | 6/1984 | Takata et al. | 204/403 |

OTHER PUBLICATIONS

Fumio Gotoh et al., Medical Research Engineering, pp. 13–19, Second Quarter, (1966).

*Primary Examiner*—G. L. Kaplan
*Attorney, Agent, or Firm*—Krass & Young

[57] ABSTRACT

A clinical chemistry analyzer system for blood chemistry analysis is disclosed. Two major parts comprise the system. One part is a discardable sensor cartridge which contains a bank of sensors, calibration fluid containers, conduit means and an external peristallically pumpable tube section. The other part is an analysis machine which interfaces with the discardable cartridge and has means to drive the peristaltic pump as well as means to interface with the sensors of the cartridge to provide a readout therefrom. The system is adapted to be made part of a heart/lung machine sustaining a patient in order to sample and monitor the venous and arterial blood flow thereof.

17 Claims, 4 Drawing Sheets

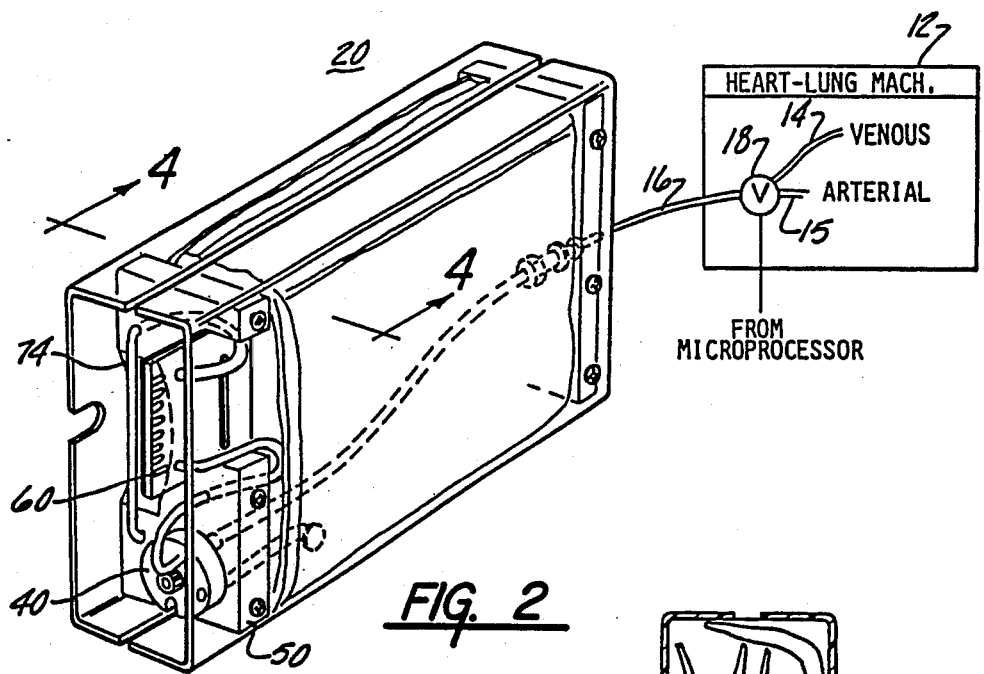
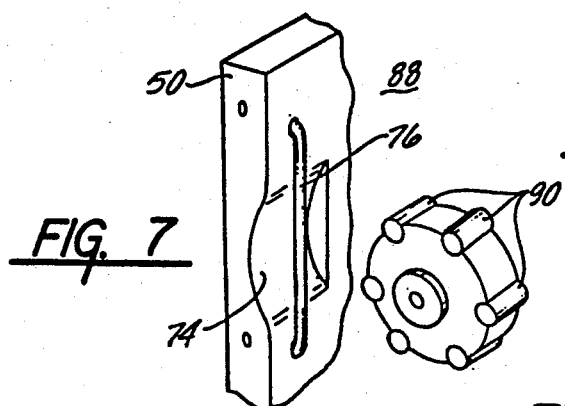
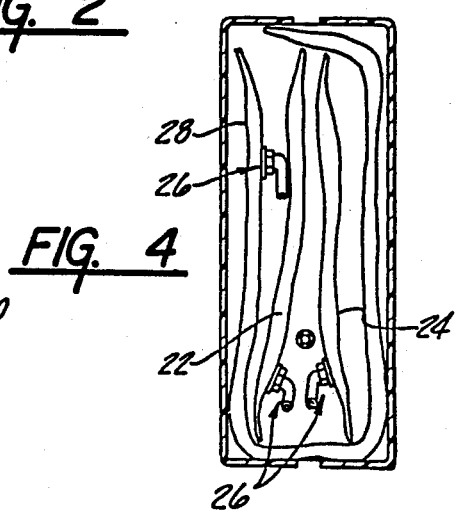
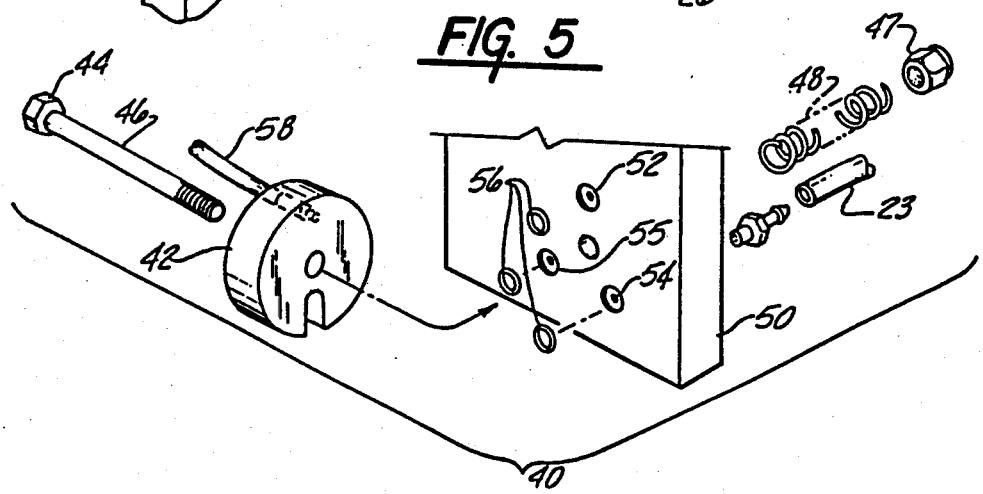

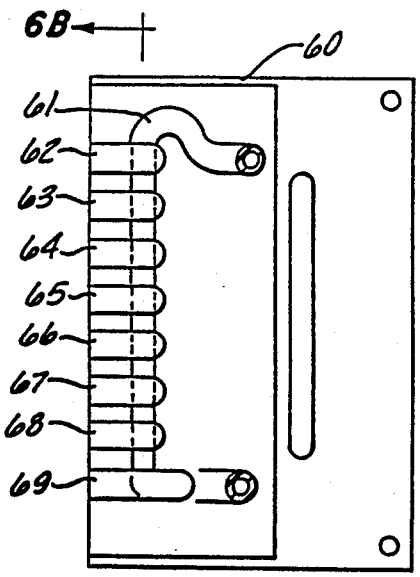
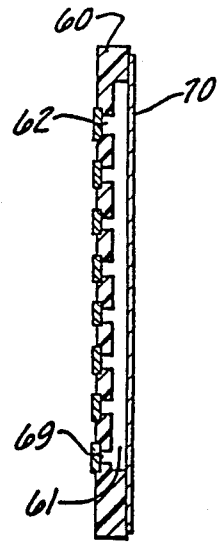
FIG. 6A  FIG. 6B
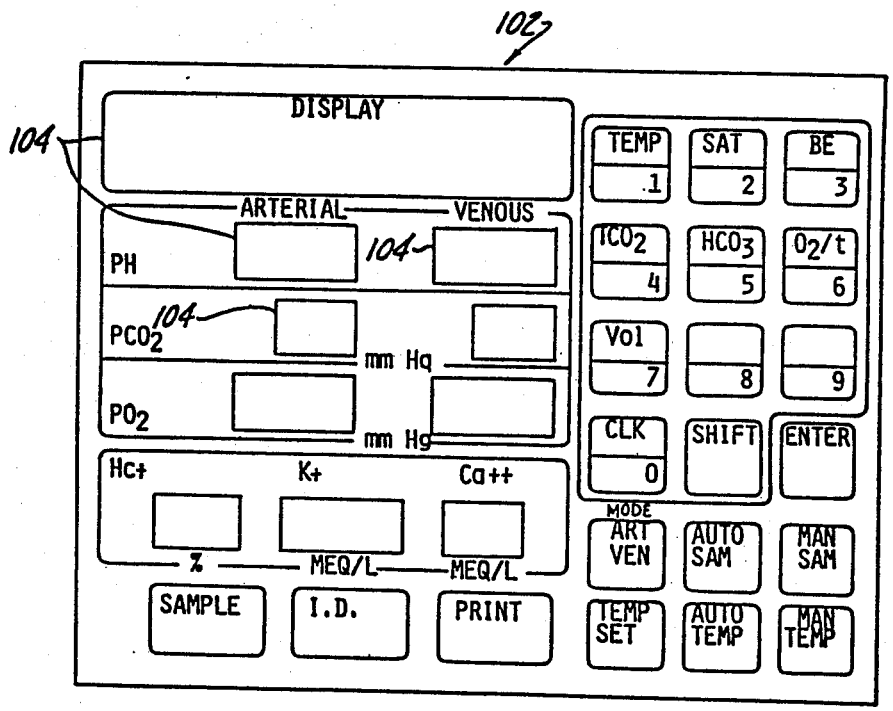
FIG. 9

APPARATUS FOR CHEMICAL MEASUREMENT OF BLOOD CHARACTERISTICS

This application is a continuation of Ser. No. 770,740 filed on Aug. 29, 1985 and now abandoned which in turn was a continuation-in-part of application Ser. No. 713,435 filed Mar. 19, 1985 and now abandoned.

FIELD OF THE INVENTION

This invention relates to apparatus for measuring certain characteristics of a blood sample and more particularly to such apparatus which employs a disposable cartridge containing a bank of sensors for such characteristics and reagents used to calibrate the sensors.

BACKGROUND OF THE INVENTION

In a variety of clinical situations it is important to measure certain chemical characteristics of the patient's blood such as pH, concentrations of calcium, potassium ions and hematocrit, the partial pressure of $O_2$ and $CO_2$ and the like. (See, for example, Fundamentals of Clinical Chemistry, Tietz, Editor, page 135 et seq., Electrochemistry; page 849 et seq., Blood Gases and Electrolytes; 1976, Saunders Company, Phila.) These situations range from a routine visit of a patient in physician's office of monitoring during open-heart surgery and the required speed, accuracy and similar performance characteristics vary with each situation.

Measurement of chemical characteristics of blood during open-heart surgery provides the most demanding set of criteria. Presently, blood gas analysis during major surgery is provided by repeated transfer of discrete blood samples to a permanent lab-based blood gas analyzer or by use of sensors placed in-line with the extra-corporeal blood circuit of a heart-lung machine employed to bypass the patient's heart.

The transfer of discrete blood samples, required by blood-gas analyzers inherently increases the risk of contaminating the blood sample with ambient air, which may alter certain of the monitored characteristics. Additionally, since such analyzers are complex and costly devices, they are typically located only in the hospital lab where they need to be operated by a skilled technician, resulting in undesirable delay during surgery, critical care or intensive care. Further, such analyzers employ bubble tonometers to generate a suitable electrolyte referent mixture by dissolving quantities of gases, stored in pressurized free-standing tanks, into the electrolyte solution. While replacement of these gas tanks is infrequently required, it is a cumbersome procedure. Finally, these existing analyzers require cleaning to decontaminate all exposed portions from the prior patient's blood prior to subsequent use.

Although use of in-line sensors minimizes the risk of contamination during transfer and of delay, they have a response which normally varies or "drifts" during use; moreover, this drift is not at a constant rate. Present in-line sensors can only be calibrated before they are placed in the extra-corporeal circuit. Thus, the inherent drift of these in-line sensors cannot be monitored, resulting in readings of ever decreasing reliability as time passes.

SUMMARY OF THE INVENTION

The present invention is directed to a system which provides quick, on-site contemporaneous blood chemistry analysis, with minimal risk of contamination, and which maintains its accuracy over its useful life.

While these characteristics are desirable in machines for use in a wide variety of applications, a blood chemistry analysis machine forming a preferred embodiment of the present invention is adapted to be connected to an extracorporeal shunt or an ex vivo blood source such as a heart/lung machine used to sustain a patient during surgery, intensive care, critical care and the like, to allow small test samples of flowing live ex vivo blood to be diverted off-line from either the venous or arterial flow lines of the heart/lung machine directly in real time to a chamber exposed to a bank of solid state micro-electrodes which generate electrical signals proportional to chemical characteristics of the real time flowing blood sample.

The bank of electrodes is housed in a disposable cartridge, adjacent to a thermal plate which maintains the test sample at a constant temperature. Upon insertion of the cartridge into a suitably adapted blood chemistry analysis machine, the electrodes connect to an electrode interface which selects one of the plurality of electrical signals generated by the sensors and passes the selected signal to a microprocessor in the machine where it is converted from analog to digital form suitable for analysis, storage and display.

A metal plate in the cartridge connects to a thermal unit in the machine which monitors the temperature of and generates and transmits heat to the plate and through it of the sample in the adjacent electrode chamber in order to maintain the sample at a constant temperature.

The cartridge also contains at least one, and preferably two containers of reference or calibrating electrolyte solution (i.e., solution serving for purposes of quality control including calibration, sometimes referred to hereinafter as control or calibration solution), as well as a reservoir suitable to collect waste fluids following assay. Upon insertion of the cartridge, a selection valve in the cartridge connects to a shaft in the machine, controlled by the microprocessor, to selectively allow either of the calibrating solutions or the test sample to flow across the electrodes.

The forces driving the fluid flow through the cartridge is provided by a peristaltic pump formed when a set of rotatable drive rollers in the machine pinch exposed portions of tubing against the curved wall of the pump slot on the cartridge. The rotation of the rollers forces either the calibrating solutions or a test sample from their respective sources through the cartridge tubing across the electrode chamber and into the waste collection reservoir. The rotation of the drive rollers is controlled by the microprocessor.

In addition to the features already mentioned, the analysis machine houses an internal digital clock which provides a time base for the operation of the system, a back-up battery power source, an operator keyboard, a display and a printer.

In operation, after all connections are suitably made, the selection valve and drive rollers cooperate to cause the calibrating solution to flow into the electrode chamber where a reading is taken and stored in the microprocessor. Subsequently and in a similar manner, a reading of the test sample is taken, analyzed by the microprocessor and displayed. The assayed fluids are directed into the waste collection reservoir. The microprocessor controls and repeats this cycle of calibration and test sample assay at a rate preselected and entered by the operator through the control keyboard. The keyboard also allows the operator to take an immediate assay at any time, even while the machine is in its automatic cycle mode, limited only by the recycling time of between two and three minutes. Following surgery, the cartridge and the tubing connecting the venous and arterial flows of the heart-lung machine to the cartridge are discarded and the machine is ready for use with a new cartridge. In that sense the cartridge is adapted for "single use" as that term is used hereinafter, although a series of assays may be made during that use. The cartridge of the present invention distinguishes in this manner from prior art cartridges designed to be discarded after a single assay.

BRIEF DESCRIPTION OF THE DRAWINGS

These and other objects and advantages of the present invention will be more apparent upon reading the following specification and by reference to the drawings in which:

FIG. 2 is an elevated side view of one embodiment of the cartridge useful with the system of FIG. 1; showing the insertion end of the cartridge in the foreground;

FIG. 4 is a side view of the trailing end of this embodiment of the cartridge;

FIG. 5 is an exploded view of the selection valve contained in this embodiment of the cartridge;

FIG. 6a is a frontal view of the electrode card contained in this embodiment of the cartridge;

FIG. 6b is a cross sectional view of this electrode card; and

FIG. 7 is a fragmentary side view of the end wall at the insertion end of this embodiment of the cartridge, showing the peristaltic pump slot;

FIG. 9 is a frontal view of one embodiment of the control panel of the blood gas analysis machine showing the display and keyboard.

DESCRIPTION OF THE PREFERRED EMBODIMENT

While the apparatus for chemical measurement of blood characteristics of the present invention may be used in a variety of clinical and experimental environments, the preferred embodiment of the invention is described as being used in major surgery. This description should not be taken to limit the applicability of the present invention.

Figure 1:
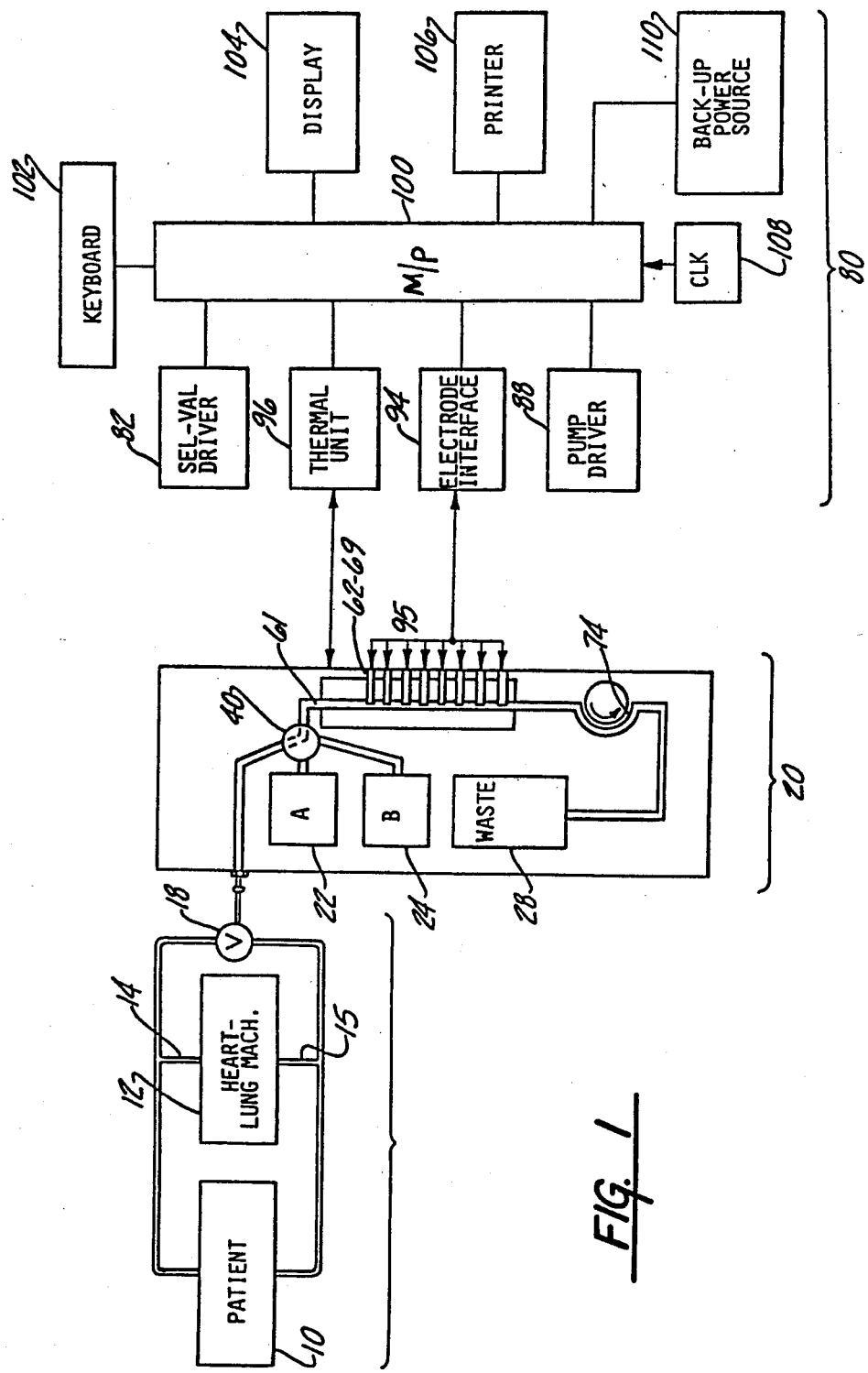
FIG. 1 is a schematic diagram showing the major components of a preferred embodiment of a blood gas analysis system.

FIG. 1 shows in schematic form a blood gas analysis system suitable for use during surgery in which a patient 10 is sustained by a heart/lung machine 12. This system allows a test sample of blood to be diverted from either the venous flow 14 or the arterial flow 15 of the heart-/lung machine 12, as selected by the system using a two-way valve 18, directly to a cartridge 20 containing a bank of sensing electrodes 64–69. These electrodes 62–69 generate electrical signals proportional to distinct characteristics of the blood sample. These signals are transmitted to a microprocessor 100, contained within a blood chemistry analysis machine 80 into which the cartridge 10 has been inserted. After analyzing these signals, microprocessor 100 controls a display 104 to display the values of these parameters of the blood sample to provide the surgeon with information on the status of the patient 10.

The system operator uses a keyboard 102 to program microprocessor 100 with the desired frequency of assays to be made by the system during surgery. The microprocessor 100 then controls the selection valve driver means 84 in machine 80 to cooperate with a selection valve 40 in cartridge 20 to allow the sequential flow flow from a calibrating solution bag 22 and a calibrating solution bag 24, both contained in cartridge 20, and then from the venous flow 14 or arterial flow 15, into electrode channel 61 exposed to electrodes 62–69. The distinct reference solutions from bags 22 and 24 provide a two-point calibration of the electrodes 62–69. In a similar manner, at the selected intervals, subsequent assays of blood samples are made, most preceded by one-point calibration, with occasional two-point calibration made to ensure continued accuracy. Upon completion of the surgery or depletion of the calibrating solutions, the cartridge 20 is discarded and replaced by a new cartridge 20 for subsequent use of the system.

All of these features and additional features are explained more fully herein.

The Cartridge And Reference Solutions; Blood Facsimile Reference Solution

Figure 3:
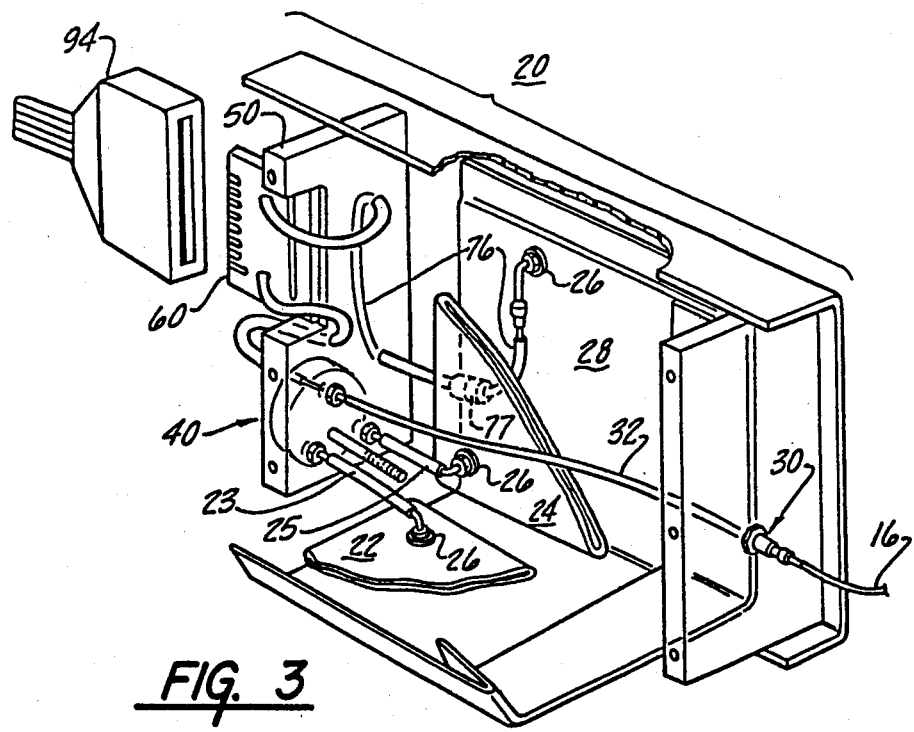
FIG. 3 is a fragmentary perspective view of this embodiment of the cartridge.

Referring now to the FIGS. 2 and 3, there is shown a box-like cartridge 20 which is preferably made of rigid plastic. The dimensions of the cartridge allow insertion into a blood gas electrolyte analysis machine 80, shown in FIG. 1, appropriately engaging features to be described herein.

The main body of cartridge 20 is partially enclosed to provide protection of its contents, flexible bags 22, 24, and 28. Calibrating solution bags 22 and 24 contain solutions and dissolved gases therein that preferably are specially formulated as described hereinafter, having known, distinct electrochemical characteristics. For a description of the technology of packaged reference or calibration solution, see U.S. Pat. No. 4,116,336. The third bag 28 is a waste collection bag which begins in an empty state and is intended to collect waste calibrating solution and blood products following assays. Preferably, calibrating solution bags 22 and 24 are encircled by the two sides of waste collection bag 28, as shown in FIG. 4.

The Reference Solutions

The bags 22 and 24 each are gas impermeable and contain an aqueous reference (i.e., calibration or control) solution (a solution electrochemically resembling blood with respect to dissolved gas and electrolyte) having known values of the chemical characteristics over a range of values that the system is intended to monitor. The values of those characteristics are different in the two bags so that by sequential passage of the two calibrating solutions over the electrodes 62–69, a two point calibration or bracket (e.g. high and low) calibration of the measurement characteristics of the electrodes may be made.

In order to maintain the concentration of gases, such as oxygen and carbon dioxide, at a known constant level in the bags 22 and 24, independent of variations in ambient pressure and temperature, the gases are added to the solutions, during their packaging, in a special manner.

As a feature of the invention, the packaging in one embodiment to be described is performed under conditions of pressure and temperature which are different from those that will be encountered during normal use of the solutions, so that advantageously the solutions may be fully saturated with the gases at the time of packaging with the important but hitherto unrealized result that these same solutions will be suitably unsaturated during use. Typically, both the temperature will be higher and the ambient pressure lower during the packaging procedure than will ever be encountered in use. For example, for a blood facsimile formulation tonometered with oxygen, $CO_2$ and nitrogen packaging may occur at a pressure in the range from about 0.80 (612 mm Hg) to about 0.95 atmospheres, and preferably from about 0.86 to about 0.92 atmospheres, and at temperatures in the approximate range from 45° to 50° C. During packaging the liquids are fully saturated with the gases and the packages are sealed in an effort to minimize entrapped air. It is found that when the temperature and ambient pressure are at normal use values, the solutions will not be saturated but their analyte concentrations will still be at the known values achieved during initial filling process. Since the solutions are unsaturated, there is no tendency for the gases in the solution to outgas into any gas bubbles formed during use.

By way of illustration but without limitation, a preferred embodiment of reference solutions for dual monitoring as described above, comprises the following solutions designated A and B and their respective methods of tonometry.

FORMULATIONS AND TONOMETRY PROCEDURE

Calibration Reference Solution A: $Na^+$, $Ca^{++}$, $pCO_2$, pH

Prepared at 37° C. and at atmospheric pressure tonometered with 8% $CO_2$—$N_2$ gas.

All compounds are weighed, combined, and diluted to volume except the calcium salt which is added after tonometering has started.

| COMPOUND | CONCENTRATION | MASS. 1.0 L |
|---|---|---|
| Buffer 3-Morpholinopropane-sulfonic Acid (MOPS) | 14.0 mmol/l | 2.926 g |
| Buffer, NaMOPS | 36.0 mmol/l | 8.316 g |
| Buffer, $NaHCO_3$ | 14.5 mmol/l | 1.218 g |
| NaCL | 110 mmol/l | 6.430 g |
| $NaN_3$ | .01% w/w | .007 g |
| KCl | 6.0 mmol/l | .447 g |
| $CaCL_2.2H_2O$ | 1.25 mmol/l | .184 g |
| 1.0N HCl | ca 8 mmol/l | ca 8 ml |
| 25 wt. % Surfactant (BRIJ 35) aq. soln. | | |

This gives parameter levels of:

| pH | $PCO_2$ mm Hg | $PO_2$ mm Hg | $K^+$-Radiometer (mmol/l) | $K^+$-Beckman (mmol/l) | $Ca^{++}$ |
|---|---|---|---|---|---|
| 7.330–7.345 | 15.5–19.0 | 116–120 | 5.6–5.8 | 5.60–5.75 | .85–.95 |

Calibration Reference Solution B: $Na^+$, $Ca^{++}$, $PO_2$, $PCO_2$, pH

Prepared at 50° C. and at 700 mm Hg absolute pressure tonometered with 21% $O_2$—4% $CO_2$—$N_2$ gas.

All compounds except the calcium salt are weighed, transferred and combined, and diluted to volume with $H_2O$. The calcium salt is added after tonometering has started.

| COMPOUND | CONCENTRATION | MASS. 1.0 L |
|---|---|---|
| Buffer: Imidazole | 50 mmol/l | 3.405 g |
| $Na_2SO_3$ | 10 mmol/l | 1.260 g |
| $NaHCO_3$ | 11.5 mmol/l | 0.966 g |
| NaCl | 93 mmol/l | 5.44 g |
| $NaN_3$ | .01% w/w | .007 g |
| KCl | 2.0 mmol/l | .149 g |
| $CaCl_2.2H_2O$ | 0.25 mmol/l | .037 g |
| 1.0N HCl | 23 mmol/l | 23 ml |
| 25 wt. % Surfactant (BRIJ 35) aq. soln. | 0.25 ml/l | |

This gives parameter levels of:

| pH | $PCO_2$ mm Hg | $PO_2$ mm Hg | $K^+$-Radiometer (mmol/l) | $K^+$-Beckman (mmol/l) | $CA^{++}$ |
|---|---|---|---|---|---|
| 6.890–6.910 | 44–48 | 0.0 | 1.8–1.9 | 1.83–1.98 | .18–.22 |

Thus the reference solution in packaged form for use in blood/gas measuring or monitoring equipment according to a preferred embodiment of the invention comprises a flexible gas-impermeable void-free package of an aqueous solution electrochemically resembling arterial blood or venous blood. The solution contains electrolyte (ionic potassium and calcium) and dissolved gas at known partial pressure. The mentioned packaged solution may thus be regarded as an electrochemical facsimile of blood in a stable form such as that exemplified by reference solution B above. The total gas pressure in the packaged solution is in the range from about 0.80 to about 0.95 atmospheres at use temperature, i.e., temperature encountered during storage and monitoring. The package may be a flexible bag, as indicated, or other suitable container package.

It is found that the preparation of the above-mentioned packaged blood facsimile involves previously unrealized compatibility problems. In this regard, when constituting the solution by conventional tonometry procedures, one finds that the compounds are incompatible in that ionic calcium separates unmanageably from the solution as a non-ionic precipitate.

Therefore, another preferred aspect of the invention resides in a method of producing a packaged blood facsimile reference solution containing oxygen gas, carbon dioxide gas and ionic potassium and calcium, without the unwanted precipitation of calcium. The method comprises constituting an aqueous buffered solution containing ionic sodium at a predetermined concentration, subjecting the resulting solution to tonometry with the gases, and following initiation tonometry admitting ionic calcium in predetermined amount with the tomometered solution, whereby the resulting solution is stable with respect to the desired ionic parameters and the solution can be suitably packaged.

Still another preferred method aspect of the invention concerns a method of producing a package of an electrochemically stable tonometered blood facsimile solution, as indicated, for storage and for use in blood/gas monitoring at normal atmospheric pressure. The method comprises packaging the solution in a sealed flexible gas-impermeable envelope free of voids (i.e., zero head space) while maintaining the solution at subatmospheric pressure and at temperature higher than said use temperature, as described hereinbefore. The packaging can be done in any suitable way by packaging art means which per se may be conventional.

A preferred embodiment of the package aspect of the invention concerns a flexible gas-impermeable package. The package contains a blood facsimile reference solution for use in blood gas electrolyte analysis, comprising ionic potassium and calcium and tonometered with oxygen and carbon dioxide, the package contents being entirely liquid and free of voids or bubbles under conditions of use.

Both calibrating solution bags 22 and 24 contain tube fittings 26, as shown in FIGS. 3 and 4, which connect in turn to calibrating solution tubes 23 and 25 respectively. Calibrating solution tubes 23 and 25 subsequently connect to selection valve 40 as described later.

Waste collection bag 28, suitable for collection of waste blood products and calibrating solutions following assay, is formed of a material which is semi-permeable to gases but impermeable to the liquid component of blood and to the calibrating solutions. It is thus intended that only the liquid component of blood and of the calibrating solution will occupy space in waste collection bag 28. In the preferred embodiment, bags 22, 24 and 28 are contained in the main body of cartridge 20 such that as waste collection bag 28 fills, it will occupy the space created by the emptying of calibrating solutions bags 22 and 24.

Waste collection bag 28 also has a tube fitting 26, shown in FIG. 4, connected to a waste tube 76, which originates at the discharging end of electrode card 60. A check valve 77 (FIG. 3) is disposed in the flow line to the collection bag 28 to prevent back-flow.

The trailing end of cartridge 20 which is inserted into blood gas analysis machine 80, contains a blood intake port 30, shown in FIGS. 2 and 3, connected by tubing 16 to either the venous blood flow 14 or the arterial blood flow 15 of a heart/lung machine 12 used to sustain the patient 10 during surgery. The system operator controls the selection of a blood sample from either the venous flow 14 or the arterial flow 15 by use of a valve 18 in tubing 16. Blood intake port 30 is connected by blood intake tube 32, passing through the interior of the cartridge 20 between bags 22 and 24, to selection valve 40 at the insertion end of cartridge 20.

As shown in FIGS. 2, 3 and 6B, the insertion end of cartridge 20 includes a selection valve 40, an electrode card 60, a peristaltic pump slot 74, and a metal plate 70. In the preferred embodiment, this insertion end of cartridge 20 is protected by the overhanging sides and top of the plastic encasing material of cartridge 20 but is exposed to the connecting portions of blood gas analysis machine 80.

Referring to FIGS. 2 and 3, selection valve 40, electrode card 60, and peristaltic pump slot 74 are all intended to connect with appropriate contacts in blood gas analysis machine 8. Insertion end wall 50, formed of plastic, serves to provide partial protection to the bags inside the main body of cartridge 20, and to provide well-positioned contact between the appropriate portions of cartridge 20 and blood gas analysis machine 80 upon insertion of the former.

As shown in FIG. 5, the selection valve 40 has a rotating plug 42, formed of a thick ring of plastic, which houses the electrode input tube 58, running ultimately to the input end of electrode channel 61. Rotating plug 42 is held flush against insertion end wall 50 by a bolt 46 passing through the center of plug 42 and through end wall 50 into the interior of cartridge 20. As bolt 46 extends into the interior of cartridge 20, it passes through a spring 48 which seats against a nut 47 which in turn serves to seat the plug 42 flush against the head 44 of bolt 46. Spring 48 thus serves to urge rotating plug 42 against insertion end wall 50. The exterior end of the bolt head 47 is recess (e.g., Allen-recess) adapted to receive a drive shaft 84 in matching relation when cartridge 20 is inserted into machine 80.

Rotating plug 42 seats against that portion of insertion end wall 50 having three ports 52, 54 and 55. Blood sample port 52 connects in the interior of cartridge 20 to blood intake tube 32; calibration solution ports 54 and 55 connect in the interior of cartridge 20 to calibration solution tubes 23 and 25 respectively. Each end of ports 52, 54 and 55 which contacts rotating plug 42 is sealed by a rubber ring 56 to provide a leakproof connection to electrode input tube 58.

As seen in FIG. 5, selection valve 40 allows the microprocessor to direct rotating plug 42 into a position aligning electrode input tube 58 with either blood intake tube 32, calibrating solution tube 23, or calibrating tube 25; when aligned with one of these tubes, rotating plug 42 blocks the flow from the other two tubes.

Another feature of the insertion end of cartridge 10 is the electrode card 60, best shown in FIGS. 6a and 6b. The electrode card 60 is formed of polyvinylchloride in a generally rectangular shape and contains a bank of electrodes 62–69. Electrode card 60 is fastened to the insertion end wall 50 such that the electrode bank protrudes and connects with an electrode interface 94, within blood gas analysis machine 80.

Preferably, each of the electrodes 62–69 are distinctly formed planar solid state electrodes which allow assay of different characteristics of human blood. The distinct construction of each electrode 62–69 produces a plurality of voltages or currents proportional to different chemical characteristics of a test sample. Electrodes 62-69 are formed in preformed circular slots in electrode card 60. These solid state electrodes may be either of the ion-selective membrane type, as is preferable, of the metal/metal-oxide type or of polarographic type, as is also preferable, all well known to the prior art. Once electrodes 62-69 are formed, their interior analyte sensing ends remain exposed to an electrode channel 61 and to any sample contained therein. Electrode channel 61 is connected at one end to the electrode input tube 58 and at the other end to waste tube 76 and is adapted to contain a sample being exposed to the electrodes 62-69. In one preferred embodiment the flow path of the electrode channels is rectilinear in cross-section (e.g., 1 mm×2 mm) having a total volume of ca. 80 μl.

Electrode card 60 is backed by a metal plate 70 disposed adjacent the electrode channel 61 which makes contact with a thermal unit 96 in machine 80, allowing the microprocessor 100 to monitor and control the temperature of the sample while in channel 61.

The exterior end of each of electrodes 62-69 is topped with an electrically conductive material. This conductive material is then drawn out to the distal end of electrode card 60 to complete, upon insertion of cartridge 20, the contact between the electrodes assaying the sample and electrode interface 94 which connects to the microprocessor 100 contained in machine 80. Microprocessor 100 is programmed to monitor, store, and display the assay results, among its other functions.

FIG. 7 illustrates the peristaltic pump slot 74 which is disposed in the insertion end of cartridge 20. Peristaltic pump slot 74 is a concave a slot in insertion end wall 50. The waste tube 76 running from the output end of channel 61 to bag fitting 26 of waste collection bag 28 is brought out of the main body of cartridge 20 through insertion end wall 50 and suspended across the peristaltic pump slot 74. Upon insertion of cartridge 20, drive rollers 90 in machine 80 pinch the exposed portion of waste tube 76 against the concave wall of the slot 74. The rotation of the rollers 90 thus forces the test sample across channel 61 of electrode card 60, through waste tube 76, and into waste collection bag 28.

The Blood Chemistry Analysis Machine

In the preferred embodiment, blood gas analysis machine 80 houses a selection valve driver means 84, a peristaltic pump driver means 88, thermal unit 96, an electrode interface 94, microprocessor 100, an operator keyboard 102, a printer 106 and a display 104, an internal digital clock 108, and back-up power source 110, as seen in the schematic diagram of FIG. 1.

Power is provided to blood gas analysis machine 80 by connection to a standard electrical outlet. A back-up power source 110, comprising a standard battery device which can power the system to maintain calibration for up to 30 minutes, is contained within machine 80.

Internal digital clock 108 contained in machine 80 is of standard design and provides a time base for the operation of the system.

Figure 8:
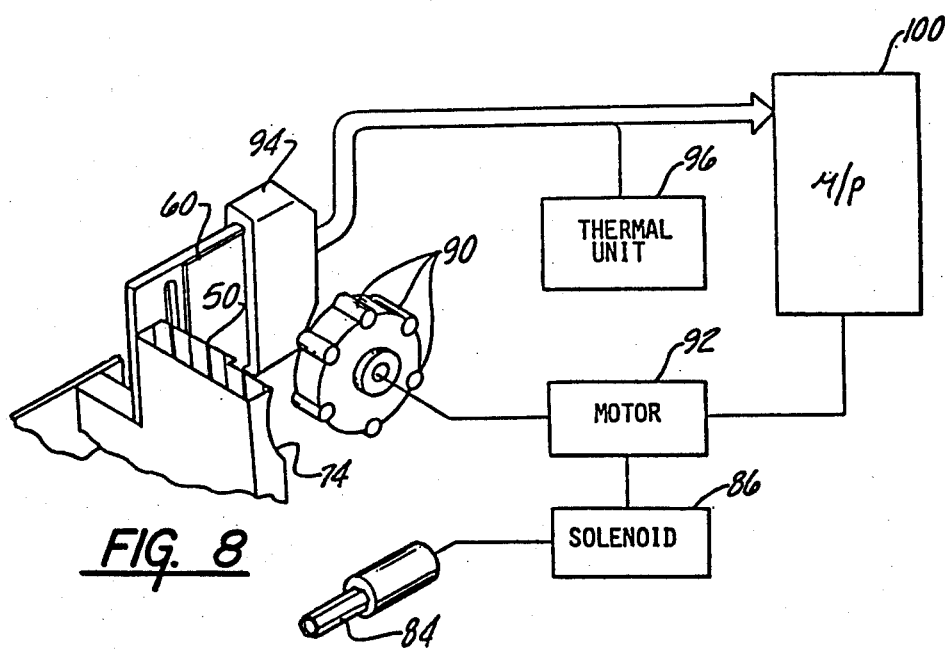
FIG. 8 is an elevated side view of that portion of the blood gas analysis machine useful with the system of FIG. 1, adapted to receive and connect suitably to certain features of this embodiment of the cartridge.

The valve driver means 82, shown in FIGS. 1 and 8, which selectively directs either calibrating solutions or test sample solution to electrodes 62-69, preferably includes a rotatable shaft 84 which fits into the end of the bolt 46 of selection valve 40. The position of the shaft 84 is controlled by the microprocessor 100 through a solenoid 86.

The peristaltic pump driver means 88, shown in FIGS. 1 and 8, which drives the fluid flow through cartridge 20 comprises rotatable peristaltic pump driver rollers 90 which contact a portion of waste tube 76 suspended across peristaltic pump slot 74 when cartridge 20 is inserted into blood gas analysis machine 80. The rotation of driver rollers 90, powered by a motor 92, is controlled by microprocessor 100.

The thermal unit 96 includes a resistance heater and thermistor which are controlled by microprocessor 100 to obtain a constant, predetermined temperature of samples in electrode channel 61. Heat generated by thermal unit 96 is conducted to metal plate 70 adjacent channel 61.

The electrode interface 94, within machine 80, connects to electrodes 62-69 when the cartridge 20 has been inserted and selects one of the plurality of signals generated by the electrodes 62-69. This selected signal passes through to microprocessor 100 which converts the signal from analog to digital form and then further processes the signal.

Microprocessor 100 is programmed to control those means described above and to control the printer 106 and display 104; additionally, microprocessor 100 receives, analyzes, and stores calibrating and test sample signals from electrodes 62-69.

Keyboard 102 is a standard keyboard device having a touch sensitive membrane which is mounted on the front panel and has a format as shown in FIG. 9. Keyboard 102 allows the operator to initiate the input of calibrating solution or test sample solution, to enter patient and operator identification information, to initiate print or display functions, to set the clock, to set the temperature, and to enter such data.

In the preferred embodiment, the display 104 is a standard, commercially available LED device, having a format shown in FIG. 9. Display 104, controlled by microprocessor 100, provides a constant reading of pH and of $CO_2$ and $O_2$ pressures in mmHg for the last sample from both venous flow 14 and arterial flow 15, as well as the operator's choice of hemocrit, $K^+$ or $Ca^{++}$ readings of the last sample. Display 104 can also provide readings of the current temperature, oxygen saturation, base excess, total $CO_2$, bicarbonate, oxygen consumption rate, or total blood volume consumed to date, as well as the status of the back-up power system, all available at the operator's discretion.

Printer 106 is a standard printer, such as a dot matrix or thermal printer, adapted to provide a hard copy of the time, date, patient and operator ID numbers, and temperature, as well as the values of all parameters of blood characteristics which can be displayed by display 104, as described above.

Operation

In operation, power is provided to a blood chemistry analysis machine 80 and a cartridge 20 is inserted therein. Blood intake valve 30 is connected by tubing 16 to the venous blood flow 14 and arterial blood flow 15 of a conventional heart/lung machine 12 sustaining a surgical patient 10. An automatically operated valve 18 allows the operator to select between the venous flow 14 or arterial flow 15. Inside cartridge 20 and passing between calibrating solution bags 22 and 24, a blood intake tube 32 connects blood intake valve 30 to a selection valve 40.

Upon insertion of cartridge 20 into blood gas analysis machine 80, a nut 47 of selection valve 40 connects to a shaft 84 in machine 80, electrode card 60 connects to electrical contacts 95 in machine 80 which lead to a microprocessor 100 contained therein, and peristaltic pump slot 74 connects to rotating drive rollers 90 in machine 90. A metal plate 70 in cartridge 20 connects to a thermal unit 96 of the machine 80, to monitor and control the temperature of samples in electrode channel 61.

To initiate the automatic cycle of periodic analyses of the blood samples, the operator uses a keyboard 102 to enter the desired frequency of assays into microprocessor 100. Microprocessor 100 then directs shaft 84, which is in contact with nut 44, to rotate a plug 42 of a selection valve 40, aligning an electrode input tube 58 with the calibrating solution ports 54 or 55. Port 54 is connected by tubing to calibrating solution bag 22; port 55 is connected to calibrating solution bag 24. The microprocessor 100 selects first the calibrating solution in bag 22 and then the calibrating solution in bag 24 to establish a two-point calibration of electrodes 62-69. Once rotating plug 42 is appropriately positioned, the rotation of rollers 90 along a portion of a waste tube 76, suspended across peristaltic pump slot 74, draws the appropriate calibration solution into channel 61 of electrode card 60.

When either calibrating solution is in contact with the electrodes 62-69, a plurality of voltages or currents proportional to distinct ionic characteristics or gas concentrations of the solution pass from the electrodes 62-69 to an electrode interface 94 which selects one of the plurality of the signals. This selected signal passes to microprocessor 100 which converts it from analog to digital form. In subsequent turns, the electrode interface 94 selects each of the other voltage signals. After the two-point calibration, the microprocessor 100 causes rotating plug 42 to align electrode input tube 58 with blood sample port 52. The drive rollers 90 then draw a blood sample into channel 61, at the same time forcing the calibration solution through waste tube 76 and into waste collection bag 28. The several voltage and current signals of the blood sample are measured, the distinct parameters are valued according to the two-point calibration and are displayed through appropriate means on blood gas analysis machine 80. Additionally, the values of the distinct parameters of the blood sample may be stored in microprocessor 100 for subsequent recall and display.

Constant temperature of samples in the channel 61 is insured by preprogramming microprocessor 100 to monitor and control the temperature of a metal plate 70 through a thermal contact 97. and a thermal unit 96.

The calibration solution and blood sample assay sequence is repeated at intervals previously selected by the operator. For most subsequent interval assays, a one-point recalibration of the electrodes 62-69 is made; occasionally, a two-point recalibration is initiated by microprocessor 100 to ensure continued accuracy.

Alternatively, a discrete blood sample may be connected to blood intake port 30 and subjected to the above-outlined sequence, enabling the system to operate as a standard lab-based blood gas analyzer.

Following the exhaustion of calibrating solutions or following the termination of the surgical procedure of a particular patient, spent cartridge 20 may be discarded and replaced with a new cartridge for subsequent use of the blood gas analysis system.

Therefore it is seen that the blood gas analysis system provides an economical, highly automated, contamination-free means to provide a surgeon with almost immediate information on the surgical patient's blood characteristics, which reflects the patient's status.

What is claimed is:

1. A clinical chemistry analyzer system for blood chemistry analysis comprising:
   (a) a sensing device or cartridge of a type that is replaceable after a single use, having a box-like body and having a fluid flow tube with a peristaltically pumpable tube section external to the body, the body being adapted to be connected for the single use by insertion in operative engagement with a blood chemistry analysis machine and to be disconnected after the single use and discarded, the body containing therein:

a container filled with a calibration liquid of known chemical characteristics;

inlet means mounted in the body to directly receive a blood sample;

a bank of reference and sensor electrodes mounted on the body, adapted to generate an electrical signal proportional to distinct chemical characteristics of the blood sample;

channel means that are open to the electrode bank and are adapted to be placed in open communication with the inlet means and the liquid container;

multi-position valve means adapted to be driven by the machine and adapted when driven to selectively direct the flow of either the calibration liquid or the blood sample over the bank of electrodes; and (b) a blood chemistry analysis machine separate from the sensing cartridge, adapted to receive and be connected to the cartridge body of replaceable cartridges of the above type in operative engagement therewith, the machine including:

valve driver means and peristaltic pump means interconnecting with said cartridge when the cartridge is inserted into the machine, the valve driver means being adapted when so connected to control the position of the cartridge valve means for selectively directing the flow of either calibration liquid or the blood sample over the bank of electrodes, the peristaltic pump means when so connected being adapted to contact the pumpable tube section of the fluid flow tube in pumping relation to cause resultant flow of fluid in the tube; and means including an electrode interface for electrical connection with the electrode bank of the body when inserted to receive and analyze electrical signals generated by the bank of electrodes upon exposure to the calibration liquid or the blood sample.

2. The system of claim 1 wherein the liquid container is a gas-impermeable foil bag.

3. The system of claim 1 wherein the cartridge body contains therein a second container filled with a calibration liquid of known chemical characteristics distinct from those of the calibration liquid contained in the first container and further wherein the valve means and valve driver means are adapted to control the valve for selectively directing the flow of calibration fluid from the second container over the bank of electrodes.

4. A clinical chemistry analyzer system for blood chemistry analysis comprising:
   (a) a sensing device or cartridge of a type that is replaceable after a single use, having a box-like body and having a fluid flow tube with a peristaltically pumpable tube section external to the body, the body being adapted to be connected for the single use by insertion in operative engagement with a blood chemistry analysis machine and to be disconnected after the single use and discarded, the body containing therein:

a container filled with a calibration liquid of known chemical characteristics;

inlet means mounted in the body to directly receive a blood sample;

a bank of reference and sensor electrodes mounted on the body, adapted to generate an electrical signal proportional to distinct chemical characteristics of the blood sample;

channel means that are open to the electrode bank and are adapted to be placed in open communication with the inlet means and on the liquid container; and (b) a blood chemistry analysis machine separate from the sensing cartridge, adapted to receive and be connected to the cartridge body of replaceable cartridges of the above type in operative engagement therewith, the machine including:

peristaltic pump means interconnecting with said cartridge when the cartridge is inserted into the machine, the peristaltic pump means when so connected being adapted to contact the pumpable tube section of the fluid flow tube in pumping relation to cause resultant flow of fluid in the tube; and means including an electrode interface for electrical connection with the electrode bank of the body when inserted to receive an analyze electrical signals generated by the bank of electrodes upon exposure of the calibration liquid or the blood sample.

5. The system of claim 3 or 4 wherein the second container is a gas-impermeable foil bag.

6. The system of claim 1 or 4 wherein the means to receive a blood sample is adapted to be connected either to a discrete sample or to the venous and arterial blood flow of a heart/lung machine sustaining a patient.

7. The system of claim 1 or 4 wherein the electrodes of the electrode bank have a planar, solid-state structure.

8. The system of claim 1 or 4 wherein the bank of electrodes is contained in a channeled card.

9. The system of claim 1 or 4 wherein the cartridge body contains therein a waste reservoir container adapted to receive effluent liquid from the bank of electrodes.

10. The system of claim 9 or 4 wherein the waste container is a gas-permeable bag.

11. A clinical chemistry analyzer system for blood chemistry analysis comprising:

(a) a sensing device or cartridge of a type having a box-like body and a flow tube with a peristaltically pumpable tube section external to the body, the body being adapted to be connected for a single use by insertion in operative engagement with a blood chemistry analysis machine and to be disconnected and discarded after the single use, the body containing therein:

a container filled with a calibration liquid of known chemical characteristics;

inlet means mounted in the body to directly receive a blood sample;

a bank of reference and sensor electrodes mounted on the body, adapted to generate an electrical signal proportional to distinct chemical characteristics of the blood sample;

channel means that are open to the electrode bank and are adapted to be placed in open communication with the blood sample inlet means on the calibration liquid container;

multi-position valve means adapted to be driven by the machine and adapted when driven to selectively direct the flow of either the calibration liquid or the blood sample over the bank of electrodes;

fluid conduit means interconnecting with the container of calibration liquid, the electrode bank, and the valve means;

(b) a blood chemistry analysis machine, adapted to receive and be connected to the cartridge body in operative engagement therewith, the machine including:

valve driver means interconnecting with the valve means of the cartridge when inserted into the machine to control the position of the valve means for selectively directing the flow of either the calibration liquid or the blood sample through the fluid conduit means and over the bank of electrodes; and means including a microprocessor and an electrode interface for electrical connection with the body when inserted to receive and analyze electrical signals generated by the bank of electrodes upon exposure of the calibration liquid or the blood sample.

12. The system of claim 11 wherein the means to receive and analyze electrical signals includes electrode interface means to select any one of a plurality of electrical signals proportional to distinct chemical characteristics of a test sample.

13. The system of claim 11 wherein the analysis machine includes a display means connected to the means to receive and analyze said electrical signals.

14. The system of claim 11 wherein at least a section of the fluid conduit means is resilient and the analysis machine includes fluid flow driver means adapted when in operative engagement with the cartridge to contact said flexible secton and provide a force to cause the flow of liquid through the conduit and over the electrode bank of the cartridge.

15. The system of claim 14 wherein the fluid flow driver means comprises a peristaltic pump and the cartridge is configured with a peristaltic pump slot such that when in operative engagement with the machine the peristaltically pumpable section of the fluid flow tube is in alignment with the slot for pumping contact with the rotating drive rollers of the peristaltic pump.

16. The system of claim 11 wherein the machine includes means to detect and control the temperature of a sample in contact with the bank of electrodes.

17. The system of claim 16 wherein the temperature control means comprises a metal plate, adjacent to the bank of electrodes, adapted to connect through thermally conductive contacts, to a thermal unit housed in the blood chemistry analysis machine.

* * * * *

UNITED STATES PATENT AND TRADEMARK OFFICE
CERTIFICATE OF CORRECTION

PATENT NO. : 4,786,394

DATED : November 22, 1988

INVENTOR(S) : Enzer et al

Page 1 of 2

It is certified that error appears in the above-identified patent and that said Letters Patent is hereby corrected as shown below:

Column 1, line 28, "of" should be --to--.

Column 2, line 44, "forces" should be --force--.

Column 3, line 64, "64-69" should be --62-69--.

Column 4, line 13, "flow flow from" should be --fluid flow from--.

Column 7, line 18, "iniation tonometry" should be --iniation of tonometry--.

Column 7, line 59, "solutions" should be --solution--.

Column 7, line 65, "20 which" should be --20, being the end opposite to that end of cartridge 20 which--.

Column 8, line 20, "8" should be --80--.

Column 9, line 33, "concave a slot" should be --concave slot--.

Column 11, line 67, "the" should be --this--.

Column 13, line 33, "an" should be --and--.

UNITED STATES PATENT AND TRADEMARK OFFICE
CERTIFICATE OF CORRECTION

PATENT NO.   : 4,786,394
DATED        : November 22, 1988
INVENTOR(S)  : Enzer et al It is certified that error appears in the above-identified patent and that said Letters Patent is hereby corrected as shown below:

Column 14, line 48, "secton" should be --section--.

Signed and Sealed this

First Day of August, 1989

Attest:

DONALD J. QUIGG

Attesting Officer

Commissioner of Patents and Trademarks